US012606535B2

(12) United States Patent
Thomas et al.

(10) Patent No.: US 12,606,535 B2
(45) Date of Patent: Apr. 21, 2026

(54) GAS PHASE METHODS TO EXTRACT NATURAL PRODUCTS

(71) Applicant: NATURAL EXTRACTION SYSTEMS, LLC, Boulder, CO (US)

(72) Inventors: C. Russell Thomas, Boulder, CO (US); Douglas G. Metcalf, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 721 days.

(21) Appl. No.: 17/798,035

(22) PCT Filed: Feb. 8, 2021

(86) PCT No.: PCT/US2021/017107
§ 371 (c)(1),
(2) Date: Aug. 5, 2022

(87) PCT Pub. No.: WO2021/159088
PCT Pub. Date: Aug. 12, 2021

(65) Prior Publication Data
US 2023/0076088 A1 Mar. 9, 2023

Related U.S. Application Data

(60) Provisional application No. 62/972,043, filed on Feb. 9, 2020.

(51) Int. Cl.
| | |
|---|---|
| *B01D 3/38* | (2006.01) |
| *A61K 31/00* | (2006.01) |
| *B01D 5/00* | (2006.01) |
| *C07D 311/80* | (2006.01) |

(52) U.S. Cl.
CPC .......... *C07D 311/80* (2013.01); *A61K 31/658* (2023.05); *B01D 3/38* (2013.01); *B01D 5/006* (2013.01)

(58) Field of Classification Search
CPC ......... B01D 3/38; B01D 5/006; C07D 311/80
See application file for complete search history.

(56) References Cited

U.S. PATENT DOCUMENTS

| | | | | |
|---|---|---|---|---|
| 2,347,322 A | * | 4/1944 | Jackson | A61K 36/898 |
| | | | | 426/489 |
| 2,467,435 A | | 4/1949 | Langhurst | |
| 2,805,981 A | | 9/1957 | Cavin | |

(Continued)

FOREIGN PATENT DOCUMENTS

| | | |
|---|---|---|
| CA | 2472561 A1 | 8/2002 |
| CN | 201643760 U | 11/2010 |

(Continued)

OTHER PUBLICATIONS

Benmoussa, H. et al., "Enhanced solvent-free microwave extraction of Foeniculum vulgare Mill. essential oil seeds using double walled reactor," Arabian Journal of Chemistry, 2016, vol. 12, pp. 3863-3870.

(Continued)

*Primary Examiner* — Jonathan Miller
(74) *Attorney, Agent, or Firm* — Douglas G. Metcalf

(57) ABSTRACT

This disclosure generally relates to gas-phase methods to distill molecules from a composition that is suspended in a gas.

18 Claims, 2 Drawing Sheets

(56) References Cited

U.S. PATENT DOCUMENTS

| | | | |
|---|---|---|---|
| 3,270,437 A * | 9/1966 | Castillo | B01D 11/0223 |
| | | | 34/168 |
| 3,969,196 A * | 7/1976 | Zosel | C11B 1/104 |
| | | | 568/918 |
| 4,227,997 A | 10/1980 | Shaddock | |
| 4,279,824 A | 7/1981 | McKinney | |
| 4,396,487 A | 8/1983 | Strumskis | |
| 4,752,307 A | 6/1988 | Asmus | |
| 5,002,784 A | 3/1991 | Paré | |
| 5,026,549 A | 6/1991 | Coutiere | |
| 5,043,100 A * | 8/1991 | Chang | A23B 2/733 |
| | | | 426/429 |
| 5,235,992 A | 8/1993 | Sensabaugh, Jr. | |
| 5,408,924 A | 4/1995 | Arendt | |
| 5,458,897 A | 10/1995 | Paré | |
| 6,019,819 A | 2/2000 | Williams | |
| 6,095,153 A * | 8/2000 | Kessler | A24F 40/46 |
| | | | 131/272 |
| 6,248,910 B1 | 6/2001 | Franke | |
| 6,365,416 B1 | 4/2002 | Elsohy | |
| 6,403,126 B1 | 6/2002 | Webster | |
| 6,860,998 B1 | 3/2005 | Wilde | |
| 7,001,502 B1 | 2/2006 | Satchwell | |
| 7,001,629 B1 | 2/2006 | Mengal | |
| 7,344,736 B2 | 3/2008 | Whittle | |
| 7,622,140 B2 * | 11/2009 | Whittle | B01D 11/0242 |
| | | | 426/494 |
| 7,833,298 B2 | 11/2010 | Larnholm | |
| 8,062,410 B2 | 11/2011 | Bullinger | |
| 8,329,229 B2 | 12/2012 | Gonzalez | |
| 8,343,553 B2 | 1/2013 | Hospodor | |
| 8,445,034 B1 | 5/2013 | Coles, Jr. | |
| 9,038,413 B2 | 5/2015 | Howard | |
| 9,630,894 B2 * | 4/2017 | Schonemann | C07C 29/86 |
| 9,987,567 B1 | 6/2018 | Ko | |
| 10,159,908 B2 | 12/2018 | Thomas | |
| 10,195,159 B2 | 2/2019 | Whittle | |
| 10,238,705 B2 | 3/2019 | Speier | |
| 10,413,843 B2 | 9/2019 | Ko | |
| 10,456,708 B2 * | 10/2019 | Thomas | B01D 3/343 |
| 10,596,486 B2 * | 3/2020 | Nevitt | C07D 311/92 |
| 10,617,974 B2 * | 4/2020 | Thomas | B01D 3/346 |
| 10,669,248 B2 | 6/2020 | Thomas | |
| 10,806,707 B2 | 10/2020 | Finley | |
| 10,822,320 B2 | 11/2020 | Thomas | |
| 10,881,982 B2 | 1/2021 | Thomas | |
| 11,643,402 B2 | 5/2023 | Thomas | |
| 11,702,397 B2 | 7/2023 | Thomas | |
| 12,297,181 B2 | 5/2025 | Thomas | |
| 12,420,214 B2 | 9/2025 | Thomas | |
| 2002/0139097 A1 | 10/2002 | Brilmaker | |
| 2004/0049059 A1 | 3/2004 | Mueller | |
| 2004/0147767 A1 * | 7/2004 | Whittle | A61K 36/185 |
| | | | 549/390 |
| 2004/0147769 A1 | 7/2004 | Davis | |
| 2004/0187340 A1 | 9/2004 | Chemat | |
| 2005/0042172 A1 | 2/2005 | Whittle | |
| 2005/0172802 A1 | 8/2005 | Betting | |
| 2009/0054711 A1 | 2/2009 | Lawrence | |
| 2010/0119606 A1 | 5/2010 | Whittle | |
| 2011/0133120 A1 | 6/2011 | McGhee | |
| 2012/0012002 A1 | 1/2012 | Kaneko | |
| 2012/0157719 A1 | 6/2012 | Teles | |
| 2013/0240347 A1 | 9/2013 | Hackleman | |
| 2014/0001027 A1 | 1/2014 | Balass | |
| 2014/0113010 A1 | 4/2014 | Hospodor | |
| 2014/0193303 A1 | 7/2014 | Ellis | |
| 2014/0271940 A1 | 9/2014 | Wurzer | |

| | | | |
|---|---|---|---|
| 2015/0068113 A1 | 3/2015 | Conner | |
| 2015/0252286 A1 | 9/2015 | Scialdone | |
| 2016/0038437 A1 | 2/2016 | Whittle | |
| 2016/0053199 A1 | 2/2016 | Clodoveo | |
| 2016/0228385 A1 | 8/2016 | Sievers | |
| 2016/0250564 A1 * | 9/2016 | Thomas | C11B 1/10 |
| | | | 554/8 |
| 2018/0000857 A1 | 1/2018 | Kotra | |
| 2018/0078874 A1 | 3/2018 | Thomas | |
| 2018/0125777 A1 | 5/2018 | Lindsay | |
| 2018/0296617 A1 | 10/2018 | Rivas | |
| 2019/0083902 A1 * | 3/2019 | Nevitt | B01D 11/0257 |
| 2019/0151171 A1 | 5/2019 | Johnson | |
| 2019/0151771 A1 * | 5/2019 | Thomas | C07D 311/80 |
| 2020/0390838 A1 | 12/2020 | Kotra | |
| 2023/0101492 A1 | 3/2023 | Thomas | |
| 2023/0312502 A1 | 10/2023 | Thomas | |
| 2024/0092752 A1 | 3/2024 | Thomas | |

FOREIGN PATENT DOCUMENTS

| | | |
|---|---|---|
| CN | 101553702 B | 6/2012 |
| CN | 103357193 A | 10/2013 |
| CN | 105943615 A | 9/2016 |
| EP | 2644039 A1 | 10/2013 |
| EP | 3453397 A1 | 3/2019 |
| FR | 2742358 A1 | 6/1997 |
| GB | 635121 | 4/1950 |
| GB | 2372714 A | 9/2002 |
| GB | 2400320 A | 10/2004 |
| JP | 4388715 B2 | 11/2002 |
| JP | 4849578 B1 | 1/2012 |
| WO | 2002089945 A2 | 11/2002 |
| WO | 2014000077 A1 | 1/2014 |
| WO | 2015049585 A2 | 4/2015 |
| WO | 2015070167 A1 | 5/2015 |
| WO | 2016153347 A1 | 9/2016 |
| WO | 2016161420 A1 | 10/2016 |
| WO | 2017192527 A1 | 11/2017 |
| WO | 2018009514 A1 | 1/2018 |
| WO | 2018047190 A1 | 3/2018 |
| WO | 2018102711 A1 | 6/2018 |
| WO | 2019082187 A1 | 5/2019 |

OTHER PUBLICATIONS

Filly, A et al., "Solvent-free microwave extraction of essential oil from aromatic herbs: From laboratory pilot industrial scale," Food Chemistry, 2013, vol. 150, pp. 193-198.

Kanter et al., "Qualitative determination of delta9-tetrahydrocannabinol and delta9-tetrahydrocannabinolic acid in marihuana by high-pressure liquid chromatograph," Journal of Chromatography, 1979, vol. 171, pp. 504-508.

Koturević et al., "Rapid Method for the Extraction of Cannabionoids from Cannabis Sativa Using Microwave Heating Technique," Journal of Criminalistics and Law, 2014, vol. 3, pp. 109-123.

Petrov, V.M. et al., "Microwave absorbing materials," Inorganic Materials, 2001, vol. 37, issue 2, pp. 93-98.

Veress et al., "Determination of cannabinoid acids by high-performance liquid chromatography of their neutral derivatives formed by thermal decarboxylation: I. Study of the decarboxylation process in open reactors," Journal of Chromatography, 1990, vol. 520, pp. 339-347.

Wang, Z. et al., "Improved solvent-free microwave extraction of essential oil from dried *Cuminum cyminum* L. and Zanthoxylum bungeanum Maxim," Journal of Chromatography A, 2006, vol. 1102, pp. 11-17.

* cited by examiner

GAS PHASE METHODS TO EXTRACT NATURAL PRODUCTS

CROSS-REFERENCE TO RELATED APPLICATIONS

This patent document claims priority to U.S. Provisional Patent Application No. 62/972,043, filed Feb. 9, 2020, which is incorporated by reference in its entirety.

BACKGROUND

Conventional methods to extract natural products lack significant economic pressure to drive innovation. The physics and chemistry of heterogenous mixtures of molecules were historically viewed as the most meaningful optimizable parameters. Once optimized, the incentive to minimize variance to ensure robust reproducibility stifled innovation. Natural product codices further stifled innovation by codifying both accepted manufacturing practices and measurable specifications for fungible commodities. Paradigm-shifting technology could increase the diversity of existing natural products, and increased diversity could allow new natural products that are optimized for function rather than fungibility.

SUMMARY

This disclosure generally relates to methods to distill natural products from gas-phase suspensions. Gas-phase suspensions improve energy transfer by increasing surface area, which generally improves extraction efficiency. Improved energy transfer reduces time-at-temperature, which generally protects thermolabile molecules. Improved extraction efficiency and the recovery of thermolabile molecules presents opportunities to manufacture extracts that more fully capture the molecular fingerprints of plant oils, which often improves the flavor, fragrance, or medicinal properties of a natural product. Gas-phase suspensions also allows for improved automation, for example, because the gas phase can pneumatically convey an input through an extraction machine.

DETAILED DESCRIPTION

Figure 1:
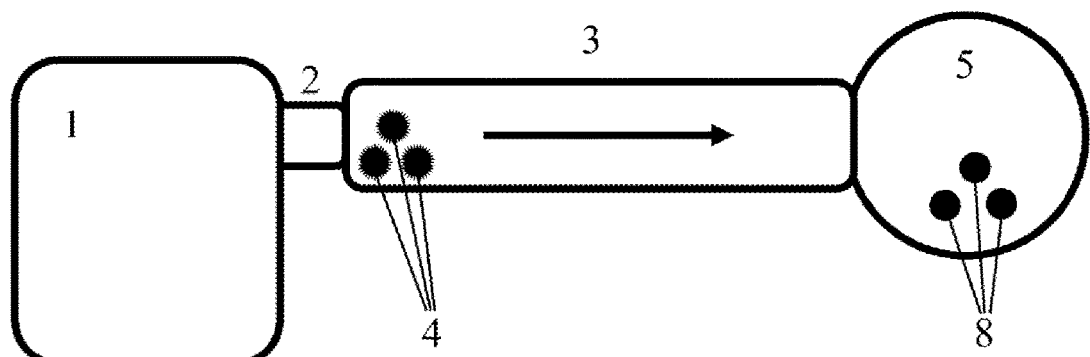
FIG. 1 is a diagram of a system to vaporize molecules from plant material using steam during proof-of-concept experiments prior to optimization on a production machine.

Various aspects of the disclosure relate to a method to separate a molecule from an impurity, comprising: providing a composition comprising the molecule and the impurity; suspending the composition in a gas to produce a suspended composition; transferring energy to the suspended composition to vaporize the molecule and produce a vaporized molecule; separating the vaporized molecule from the impurity; contacting the vaporized molecule with a heat sink to produce a condensed molecule; and collecting an extract comprising the condensed molecule.

"Comprising" and "comprises" refer to an open set, for example, such that a composition comprising a molecule and an impurity can also comprise additional chemical species.

In some embodiments, the impurity is cellulose or protein. In some specific embodiments, the impurity is cellulose, and the cellulose is cellulose I. In some very specific embodiments, the impurity is cellulose, the cellulose is cellulose I, and the cellulose I is cellulose Ibeta.

In some embodiments, the composition has a surface-area-to-volume ratio of at least 500 per meter. In some specific embodiments, the composition has a surface-area-to-volume ratio of at least 1000 per meter. In some very specific embodiments, the composition has a surface-area-to-volume ratio of at least 5000 per meter.

In some embodiments, the method comprises processing a plant material that has a surface-area-to-volume ratio of less than 500 per meter to provide the composition, wherein the processing comprises one or both of grinding the plant material and separating particles of the plant material by size.

In some embodiments, providing the composition comprises drying a starting composition to a water content of less than 20 percent by mass. In some specific embodiments, providing the composition comprises drying a starting composition to a water content of less than 10 percent by mass.

In some embodiments, transferring the energy comprises one, two, or each of convective heating, conductive heating, and radiative heating.

In some embodiments, providing the composition comprises directing the composition through an entrance to a path; and separating the vaporized molecule from the impurity comprises directing the impurity through a first exit to the path.

In some embodiments, separating the vaporized molecule from the impurity comprises directing the vaporized molecule and the impurity through a cyclone, wherein the cyclone directs the impurity through the first exit to the path.

In some embodiments, the gas propels the suspended composition from the entrance to the first exit at a velocity of at least 1 meter per second. In some specific embodiments, the gas propels the suspended composition from the entrance to the first exit at a velocity of at least 5 meters per second. In some very specific embodiments, the gas propels the suspended composition from the entrance to the first exit at a velocity of at least 10 meters per second.

In some embodiments, the suspended composition travels a distance of at least 1 meter between the entrance and the first exit. In some specific embodiments, the suspended composition travels a distance of at least 5 meters between the entrance and the first exit. In some very specific embodiments, the suspended composition travels a distance of at least 10 meters between the entrance and the first exit.

In some embodiments, the gas propels the suspended composition from the entrance to the first exit in less than 10 minutes. In some specific embodiments, the gas propels the suspended composition from the entrance to the first exit in less than 1 minute. In some very specific embodiments, the gas propels the suspended composition from the entrance to the first exit in less than 10 seconds.

In some embodiments, the method comprises directing the vaporized molecule through a second exit to the path prior to contacting the vaporized molecule with the heat sink.

In some embodiments, the gas travels from the entrance to the second exit at a velocity of at least 1 meter per second. In some specific embodiments, the gas travels from the entrance to the second exit at a velocity of at least 5 meters per second. In some specific embodiments, the gas travels from the entrance to the second exit at a velocity of at least 10 meters per second.

In some embodiments, the gas travels a distance between the entrance and the second exit of at least 1 meter. In some specific embodiments, the gas travels a distance between the entrance and the second exit of at least 5 meters. In some very specific embodiments, the gas travels a distance between the entrance and the second exit of at least 10 meters.

In some embodiments, the gas travels from the entrance to the second exit in less than 10 minutes. In some specific embodiments, the gas travels from the entrance to the second exit in less than 1 minute. In some very specific embodiments, the gas travels from the entrance to the second exit in less than 10 seconds.

In some embodiments, the path is a tube.

In some embodiments, the entrance is a combining comb of a steam injector.

In some embodiments, the gas is steam.

In some embodiments, the gas is air.

In some embodiments, contacting the vaporized molecule with the heat sink comprises directing the vaporized molecule into a liquid.

In some embodiments, the liquid is an aqueous liquid. In some specific embodiments, the liquid is water.

In some embodiments, the molecule is immiscible with water.

In some embodiments, the energy is transferred to the suspended composition to vaporize the molecule at a vaporization rate, which is an amount of moles of the molecule that are vaporized per unit time; the vaporized molecule is contacted with a heat sink to produce a condensed molecule at a condensation rate, which is an amount of moles of the vaporized molecule that are condensed per unit time; the vaporization rate is at least 50 percent of the condensation rate; and the condensation rate is at least 50 percent of the vaporization rate. In some specific embodiments, the vaporization rate is at least 80 percent of the condensation rate; and the condensation rate is at least 80 percent of the vaporization rate. In some very specific embodiments, the vaporization rate is at least 90 percent of the condensation rate; and the condensation rate is at least 90 percent of the vaporization rate.

In some embodiments, the method is operated continuously for a period of time of at least 10 minutes such that each of the providing, the suspending, the transferring, the separating, the contacting, and the collecting are performed simultaneously on different portions of the same composition. In some specific embodiments, the method is operated continuously for a period of time of at least 30 minutes such that each of the providing, the suspending, the transferring, the separating, the contacting, and the collecting are performed simultaneously on different portions of the same composition. In some very specific embodiments, the method is operated continuously for a period of time of at least 1 hour such that each of the providing, the suspending, the transferring, the separating, the contacting, and the collecting are performed simultaneously on different portions of the same composition.

In some embodiments, transferring the energy to the suspended composition comprises contacting the suspended composition with no greater than 0.04 kilowatt hours of energy per gram of the suspended composition. In some specific embodiments, transferring the energy to the suspended composition comprises contacting the suspended composition with at least 0.0004 and no greater than 0.04 kilowatt hours of energy per gram of the suspended composition. In some very specific embodiments, transferring the energy to the suspended composition comprises contacting the suspended composition with at least 0.0005 and no greater than 0.02 kilowatt hours of energy per gram of the suspended composition.

In some embodiments, transferring the energy to the suspended composition comprises contacting the suspended composition with the energy at a rate of no greater than 100 kilowatts of power per gram of the composition for a duration of no greater than 60 seconds. In some specific embodiments, transferring the energy to the suspended composition comprises contacting the suspended composition with the energy at a rate of at least 1 kilowatt and no greater than 100 kilowatts of power per gram of the composition for a duration of at least 200 milliseconds and no greater than 20 seconds.

In some embodiments, the vaporized molecule is contacted with the heat sink no greater than 10 minutes after the energy is transferred to the suspended composition. In some specific embodiments, the vaporized molecule is contacted with the heat sink no greater than 1 minute after the energy is transferred to the suspended composition. In some very specific embodiments, the vaporized molecule is contacted with the heat sink no greater than 10 seconds after the energy is transferred to the suspended composition.

In some embodiments, the composition is *cannabis*, and the molecule is a cannabinoid. In some specific embodiments, the composition is industrial hemp, and the molecule is cannabidiol, cannabidivarin, cannabigerol, or cannabigerovarin. In some specific embodiments, the composition is marijuana, and the molecule is tetrahydrocannabinol or tetrahydrocannabivarin.

In some embodiments, the composition comprises plant material obtained from the genus *Agave*; species *Agave amica*; genus *Angelica*; species *Angelica archangelica*; genus *Aquilaria*; species *Aquilaria malaccensis*; genus *Chamaemelum*; species *Chamaemelum nobile*; genus *Chamaecyparis*; species *Chamaecyparis funebris*; genus *Citrus*; species *Citrus aurantium*; genus *Coffea*; species *Coffea arabica*; species *Coffea canephora*; genus *Crocus*; species *Crocus sativus*; genus *Fucus*; species *Fucus vesiculosus*; genus *Gyrinops*; species *Gyrinops walla*; genus *Helichrysum*; species *Helichrysum italicum*; genus *Humulus*; species *Humulus lupulus*; genus *Hypericum*; species *Hypericum perforatum*; genus *Inula*; species *Inula helenium*; genus *Jasminum*; species *Jasminum multiflorum*; species *Jasminum officinale*; species *Jasminum sambac*; genus *Juniperus*; species *Juniperus mexicana*; species *Juniperus virginiana*; genus *Magnolia*; species *Magnolia alba*; species *Magnolia champaca*; genus *Matricaria*; species *Matricaria chamomilla*; genus *Melissa*; species *Melissa officinalis*; genus *Phialophora*; species *Phialophora parasitica*; genus *Plumeria*; genus *Pogostemon*; species *Pogostemon cablin*; genus *Rosa*; species *Rosa centifolia*; species *Rosa damascena*; genus *Santalum*; species *Santalum album*; species *Santalum spicatum*; genus *Theobroma*; species *Theobroma cacao*; genus *Vanilla*; or species *Vanilla* planifolia.

In some embodiments, the molecule is 3-octanone; 4-hydroxybenzaldehyde; alantolactone; alpha-cedrene; alpha-pinene; alpha-santalol; azulene; benzyl acetate; beta-caryophyllene; beta-cedrene; beta-damascenone; beta-damascone; beta-ionone; beta-phellandrene; beta-santalol;

bisabolol; borneol; cadalene; carvone; chamazulene; cedrol; citral; citronellal; citronellol; cyclopentadecanolide; euca- lyptol; farnesene; furaneol; (furan-2-yl)methanethiol; fur- fural; furfuryl alcohol; geraniol; germacrene A; germacrene B; germacrene C; germacrene D; germacrene E; guaiacol; humulene; isoalantolactone; isobutyraldehyde; isovaleralde- hyde; jasmonic acid; methyl jasmonate; limonene; linalool; linalyl acetate; 5-methylfurfural; myrcene; nerol; norpa- tchoulenol; patchoulol; rose oxide; safranal; sotolon; or valencene. In some specific embodiments, the molecule is alpha-santalol or beta-santalol.

EXEMPLIFICATION

The following examples describe commercially-relevant embodiments of the disclosure and do not limit the scope of the disclosure or any claim that matures from this patent document.

Example 1. Proof-of-Concept Distillation of Target Molecules from Plant Material without Recovery The method of Example 1 is used to determine whether the distillation of target molecules from a plant material that is suspended in a gas is commercially viable prior to optimization at scale on a production machine.

Plant material is ground to a surface-area-to-volume ratio of greater than 5000 per meter and then dried to a water content of less than 10 percent by mass. Volatile molecules are then vaporized from the ground plant material in an apparatus according to FIG. 1. The ground plant material 4 is directed into a tube 3 in fluid communication with the outlet 2 of a steam boiler 1. The tube 3 has a length of at least 1 meter. Steam is released from the steam boiler 1 to suspend the ground plant material in the steam and contact the ground plant material 4 with a known amount of energy. The steam also propels the ground plant material through the tube 3. Depleted plant material 8, which is depleted of a portion or substantially all of the target molecules, is col- lected in a gas-permeable container 5 at the end of the tube 3.

The concentration of the target molecules in the ground plant material 4 prior to extraction is compared to the concentration in the depleted plant material 8 following extraction to determine extraction efficiency. The method is repeated with different parameters to determine whether a commercially-viable extraction efficiency is achievable for the target molecules.

Figure 2:
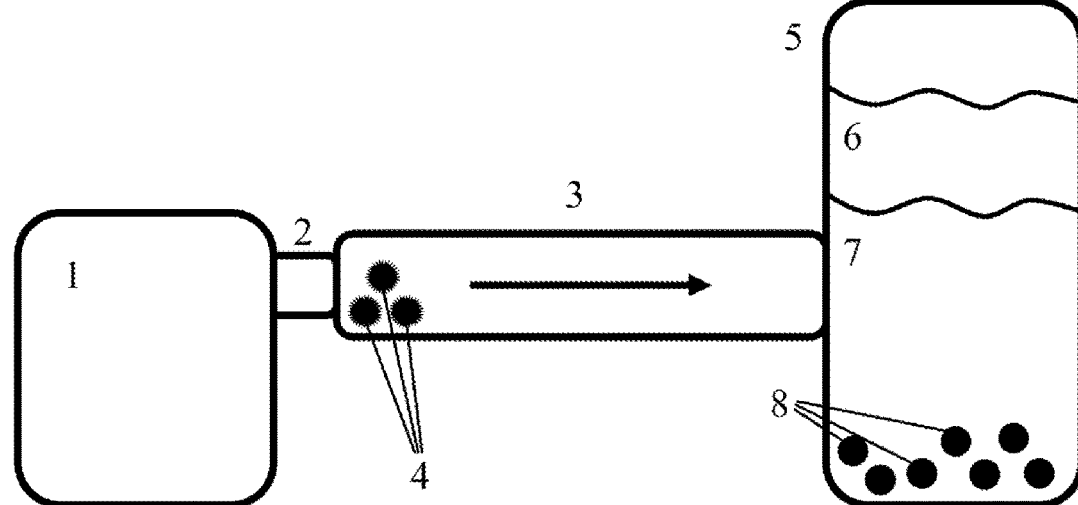
FIG. 2 is a diagram of a system to distill volatile molecules from plant material using steam.
Figure 3:
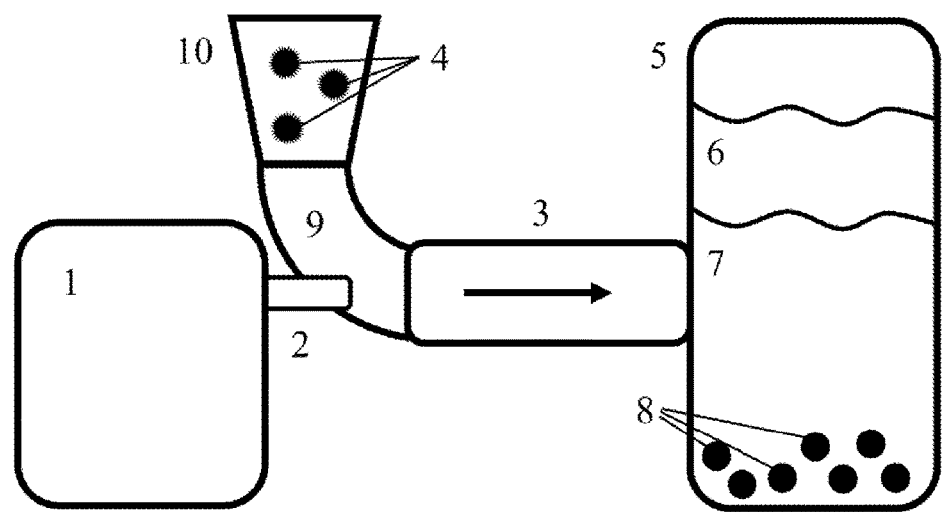
FIG. 3 is a diagram of a system to distill volatile molecules from plant material using steam, which includes a steam injector to feed plant material into the system.
Figure 4:
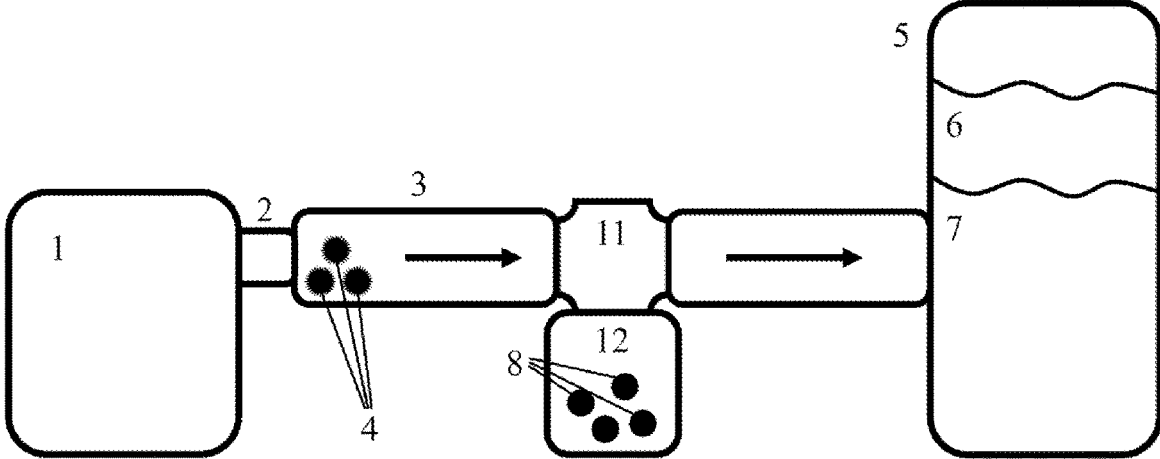
FIG. 4 is a diagram of a system to distill volatile molecules from plant material using steam, which includes a cyclone to separate depleted plant material from the steam.

Example 2. Extraction of Volatile Molecules from Plant Material with Recovery Extraction apparatuses are provided as shown in FIG. 2, FIG. 3, and FIG. 4. A steam boiler 1 is configured to heat water to a temperature of 105 to 260 degrees Celsius and produce steam having a pressure of 120 to 4000 kilopascals. Plant material is ground to a surface-area-to-volume of greater than 5000 per meter. The ground plant material is directed into a tube 3 in which the ground plant material 4 is contacted with the steam. The steam propels the ground plant material 4 through the tube 3 at a velocity of greater than 1 meter per second during which the ground plant material is contacted with 0.0004 to 0.04 kilowatt hours of energy per gram of the ground plant material 4. For example, the steam can have a temperature of 240 degrees Celsius, and the ground plant material 4 and steam can be contacted at a ratio of 1 gram of ground plant material 4 to 10 grams of steam to transfer greater than 0.0004 kilowatt hours of energy from the steam to the ground plant material 4 and result in a suspended composition comprising the ground plant material 4 suspended in the steam. The energy transfer to the ground plant material 4 results in the vaporization of volatile molecules from the ground plant material 4. The steam and volatile molecules are then directed into a liquid collection tank 5 containing water as a heat sink to condense the volatile molecules and steam. The volatile molecules form a lipid phase 6, and the steam condenses into an aqueous phase 7. The lipid phase 6 is then separated from the aqueous phase 7 to recover an extract.

FIG. 3 includes a steam injector 9, which allows a continuous feed of ground plant material 4 from a hopper 10. The steam injector 9 creates favorable pressure differentials in the apparatus to automatically feed ground plant material 4 into the tube 3.

Depleted plant material 8 is optionally directed into the liquid collection tank 5 as shown in FIG. 2 and FIG. 3. Depleted plant material 8 is alternatively directed into a waste receptacle 12 using a cyclone 11 as shown in FIG. 4.

What is claimed is:

1. A method to separate a molecule from an impurity, comprising:

providing a composition comprising the molecule and the impurity, wherein the impurity is cellulose I, and wherein providing the composition comprises directing the composition through an entrance to a path;

suspending the composition in a gas to produce a sus- pended composition that comprises the molecule and the impurity;

propelling the suspended composition from the entrance to a first exit to the path at a velocity of at least 1 meter per second;

transferring energy to the suspended composition to vaporize the molecule and produce a vaporized mol- ecule;

separating the vaporized molecule from the impurity, wherein separating the vaporized molecule from the impurity comprises directing the cellulose I through a first exit from the path;

condensing the vaporized molecule to produce a con- densed molecule; and collecting an extract comprising the condensed molecule.

2. The method of claim 1, wherein the composition has a surface-area-to-volume ratio of at least 500 per meter.

3. The method of claim 1, comprising processing a plant material that has a surface-area-to-volume ratio of less than 500 per meter to provide the composition, wherein the processing comprises one or both of grinding the plant material and separating particles of the plant material by size.

4. The method of claim 1, wherein the gas propels the suspended composition from the entrance to the first exit at a velocity of at least 1 meter per second.

5. The method of claim 1, wherein the suspended com- position travels a distance of at least 1 meter between the entrance and the first exit.

6. The method of claim 1, wherein the gas propels the suspended composition from the entrance to the first exit in less than 10 minutes.

7. The method of claim 1, comprising directing the vaporized molecule through a second exit from the path prior to contacting the vaporized molecule with the heat sink.

7

8

8. The method of claim 7, wherein the gas travels from the entrance to the second exit at a velocity of at least 1 meter per second.

9. The method of claim 7, wherein the gas travels a distance between the entrance and the second exit of at least 1 meter.

10. The method of claim 7, wherein the gas travels from the entrance to the second exit in less than 10 minutes.

11. The method of claim 1, wherein:

the energy is transferred to the suspended composition to vaporize the molecule at a vaporization rate, which is an amount of moles of the molecule that are vaporized per unit time;

the vaporized molecule is contacted with a heat sink to produce the condensed molecule at a condensation rate, which is an amount of moles of the vaporized molecule that are condensed per unit time;

the vaporization rate is at least 50 percent of the condensation rate; and the condensation rate is at least 50 percent of the vaporization rate.

12. The method of claim 11, wherein the method is operated continuously for a period of time of at least 30 minutes such that each of the providing, the suspending, the transferring, the separating, the condensing, and the collecting are performed simultaneously on different portions of the same composition.

13. The method of claim 1, wherein transferring the energy to the suspended composition comprises contacting the suspended composition with at least 0.0004 and no greater than 0.04 kilowatt hours of energy per gram of the suspended composition.

14. The method of claim 1, wherein the vaporized molecule is contacted with the heat sink no greater than 10 minutes after the energy is transferred to the suspended composition.

15. A method to separate a molecule from an impurity, comprising:

providing a composition comprising the molecule and the impurity, wherein the impurity is cellulose I; the composition has a surface-area-to-volume ratio of at least 500 per meter; and providing the composition comprises directing the composition through an entrance to a path;

suspending the composition in a gas to produce a suspended composition that comprises the molecule and the impurity;

propelling the suspended composition from the entrance to a first exit to the path at a velocity of at least 1 meter per second;

transferring energy to the suspended composition to vaporize the molecule and produce a vaporized molecule, wherein transferring the energy to the suspended composition comprises contacting the suspended composition with at least 0.0004 and no greater than 0.04 kilowatt hours of energy per gram of the suspended composition;

separating the vaporized molecule from the impurity, wherein separating the vaporized molecule from the impurity comprises directing the cellulose I through a first exit from the path;

condensing the vaporized molecule to produce a condensed molecule; and collecting an extract comprising the condensed molecule.

16. The method of claim 15, wherein:

the energy is transferred to the suspended composition to vaporize the molecule at a vaporization rate, which is an amount of moles of the molecule that are vaporized per unit time;

the vaporized molecule is condensed to produce the condensed molecule at a condensation rate, which is an amount of moles of the vaporized molecule that are condensed per unit time; and the method is performed such that the vaporization rate is at least 50 percent of the condensation rate, and the condensation rate is at least 50 percent of the vaporization rate.

17. The method of claim 15, wherein the method is operated continuously for a period of time of at least 30 minutes such that each of the providing, the suspending, the transferring, the separating, the condensing, and the collecting are performed simultaneously on different portions of the same composition.

18. A method to separate a molecule from an impurity, comprising:

providing a composition comprising the molecule and the impurity, wherein the impurity is cellulose I; the composition has a surface-area-to-volume ratio of at least 500 per meter; and providing the composition comprises directing the composition through an entrance to a path;

suspending the composition in a gas to produce a suspended composition that comprises the molecule and the impurity;

propelling the suspended composition from the entrance to a first exit to the path at a velocity of at least 1 meter per second;

transferring energy to the suspended composition to vaporize the molecule and produce a vaporized molecule, wherein transferring the energy to the suspended composition comprises contacting the suspended composition with at least 0.0004 and no greater than 0.04 kilowatt hours of energy per gram of the suspended composition;

separating the vaporized molecule from the impurity, wherein separating the vaporized molecule from the impurity comprises directing the cellulose I through a first exit from the path;

condensing the vaporized molecule to produce a condensed molecule; and collecting an extract comprising the condensed molecule, wherein:

the energy is transferred to the suspended composition to vaporize the molecule at a vaporization rate, which is an amount of moles of the molecule that are vaporized per unit time;

the vaporized molecule is condensed to produce the condensed molecule at a condensation rate, which is an amount of moles of the vaporized molecule that are condensed per unit time;

the method is performed such that the vaporization rate is at least 50 percent of the condensation rate, and the condensation rate is at least 50 percent of the vaporization rate; and the method is operated continuously for a period of time of at least 30 minutes such that each of the providing, the suspending, the transferring, the separating, the condensing, and the collecting are performed simultaneously on different portions of the same composition.

* * * * *